(12) United States Patent
Thompson et al.

(10) Patent No.: US 10,004,697 B2
(45) Date of Patent: Jun. 26, 2018

(54) IN VIVO SPERM SELECTION FOR TREATING MALE INFERTILITY

(71) Applicant: M Pharmaceutical USA Inc., Wilmington, DE (US)

(72) Inventors: Ronald J. Thompson, Cincinnati, OH (US); James M. Thompson, Cincinnati, OH (US); Gary A. Thompson, Ft. Thomas, KY (US)

( * ) Notice: Subject to any disclaimer, the term of this patent is extended or adjusted under 35 U.S.C. 154(b) by 0 days. days.

(21) Appl. No.: 15/353,130

(22) Filed: Nov. 16, 2016

(65) Prior Publication Data

US 2018/0133167 A1    May 17, 2018

(51) Int. Cl.

| | | |
|---|---|---|
| *A61K 31/045* | (2006.01) | |
| *G01N 33/50* | (2006.01) | |
| *A61K 9/00* | (2006.01) | |

(52) U.S. Cl.
CPC .......... *A61K 31/045* (2013.01); *A61K 9/0034* (2013.01); *G01N 33/5091* (2013.01); *G01N 2800/367* (2013.01)

(58) Field of Classification Search
CPC .................................................. A61K 31/045
See application file for complete search history.

(56) References Cited

U.S. PATENT DOCUMENTS

| | | |
|---|---|---|
| 4,357,934 A | 11/1982 | Fahim |
| 4,474,576 A | 10/1984 | Gobby |
| 5,879,877 A | 3/1999 | Ellington et al. |
| 6,140,121 A | 10/2000 | Ellington et al. |
| 6,171,778 B1 | 1/2001 | Ellington et al. |
| 6,224,541 B1 | 5/2001 | Thompson |
| 6,322,493 B1 | 11/2001 | Thompson |
| 6,593,138 B1 | 7/2003 | Oliver et al. |
| 6,593,309 B2 | 7/2003 | Ellington et al. |
| 6,702,733 B1 | 3/2004 | Thompson |
| 7,838,509 B2 | 11/2010 | Ellington et al. |
| 8,192,347 B2 | 6/2012 | Bollinger |
| 2005/0244520 A1 | 11/2005 | Thompson et al. |
| 2006/0249162 A1 | 11/2006 | Thompson et al. |
| 2007/0060653 A1 | 3/2007 | Thompson |
| 2011/0183934 A1 | 7/2011 | Ellington et al. |
| 2015/0190632 A1 | 7/2015 | Raviv et al. |

OTHER PUBLICATIONS

Brannigan, R; Lipshultz, L., "Sperm Transport and Capacitation", Glob. libr. women's med., ISSN:1756-2228, 2008.
Hwang, K; Lipshultz, L., Lamb, D., "Use of Diagnostic Testing to Detect Infertility", Curr. Urol. Rep. Feb. 2011; 12 (1): 68-76.

*Primary Examiner* — Zohreh A Fay
(74) *Attorney, Agent, or Firm* — Ronald J. Richter; Hasse & Nesbitt LLC (57) ABSTRACT

A composition and method are disclosed for optimizing sperm survival and function for couples suffering from male infertility by stimulating and increasing the female sexual partner's vaginal lubrication. An increased amount of vaginal transudate is produced in the female by the topical vulval application of a composition containing menthol or a related cooling compound. The resulting increased amount of vaginal transudate can support the function and viability of the spermatozoa in the hostile vaginal environment and ultimately in the cervical mucus to both capacitate sperm in vivo and to provide a medium for gradient sperm differentiation in the vagina and cervix. The inventive composition and method provides a means to compensate for male infertility caused by abnormal semen quality in order for a couple to successfully achieve conception.

5 Claims, 4 Drawing Sheets

IN VIVO SPERM SELECTION FOR TREATING MALE INFERTILITY

FIELD OF THE INVENTION

The present invention relates in general to reproductive medicine, and in particular to compositions and methods for treating male fertility problems.

BACKGROUND OF THE INVENTION

Infertility is a difficult and stressful condition for patients and treating physicians alike. Couples struggling with infertility often find that the problem is not a female issue. The failure to conceive within 1 year occurs in about 15% of couples, and male infertility is considered the causative reason in about 40% of problems related to conception. Male infertility therefore continues to be a clinical challenge of increasing significance.

Male infertility commonly refers to the inability of a male to induce pregnancy in a fertile female after a period of 12 months, without the use of contraceptives. Male infertility affects one in 20 men, with over 90% of cases caused by abnormal semen quality. Abnormal semen quality can be categorized as an abnormal sperm production with shape or motility defects, or abnormal low sperm number. Low sperm number has been defined as a decrease in the concentration of spermatozoa to below 15 million/ml, or a total number of below 39 million. Although sexual function is normal in men suffering from abnormal semen quality, there is a reduced count of normal, functional spermatozoa and/or a disproportionate number of spermatozoa that are dysfunctional in either motility or morphology.

The complex process of sperm transport through the female reproductive tract begins at the time of ejaculation. Millions of spermatozoa are deposited in the anterior vagina during coitus. A vast number of these spermatozoa are lost though the vaginal introitus, but a pool of spermatozoa, suspended in seminal fluid and vaginal plasma transudate, remain in the posterior vaginal fornix. For human males with normal sperm production, within minutes of ejaculation 1.5 ml to 5.0 ml of semen containing between 200 and 500 million sperm is deposited. Freshly ejaculated sperm are unable or poorly able to fertilize. Rather, they must first undergo a series of physiologic changes known collectively as capacitation before being capable of penetrating the egg. Capacitation occurs in vivo while the sperm reside in the female reproductive tract, and results in the spermatozoa gaining the ability to undergo fusion with the female oocyte during the acrosome reaction and subsequently proceed to fertilization. Human sperm generally require a period of several hours for capacitation to occur. Typically capacitation of spermatozoa is assisted by the sperm being suspended in a pool of seminal fluid and vaginal plasma transudate, which remains following intercourse in the posterior vaginal fornix and intermixes with endocervical mucus at the opening of the cervical os. The positioning and composition of this pool allows the sperm to capacitate and swim up into the cervical canal and the uterus, ultimately finding the oocyte for fertilization.

Male infertility resulting from an abnormal sperm quality disrupts the natural mechanism for fertilization. Sperm capacitation and fertilization are invariably unsuccessful because the number of healthy spermatozoa released into the vaginal fornix is lacking. To overcome this problem, various assisted reproduction techniques have been introduced over the last several decades, including therapeutic interventions such as artificial insemination, in vitro fertilization (IVF), gamete intrafallopian transfer (GIFT) or intracytoplasmic sperm injection (ICSI) has allowed scientists and clinicians to treat poor fertility in some individuals or to store sperm, oocytes or embryos for use at other locations or times. With these in vitro techniques, different methods may be used to isolate the healthy, motile (swimming) sperm from dead sperm, such as centrifugation, swim-up, separation columns, and the like. For example, one such method known as "sperm swim-up" isolates healthy sperm by a swim-up method. See, e.g., FIGS. 4A-4E. Briefly, sperm swim-up tubes are prepared by placing wash media in a round bottom tube. Sperm are layered under this wash media using a needle and syringe. The tubes are incubated undisturbed, and the wash medium (that the motile sperm have swum up into) is removed and centrifuged. A pellet of motile sperm is recovered, which is then layered once again under fresh wash medium for analysis or use. Other methods, such as column separation, may alternatively be used.

While the assisted reproduction technologies described above have revolutionized the treatment of infertile couples, there is still room for improvement. Although sperm can be extended in media for use in sperm analysis and diagnostic tests, existing assisted reproduction techniques generally decrease the normal survival and function of sperm. These in vitro techniques involve the sperm spending time outside of the human body, in a test tube or in culture, and can be damaging to healthy, functional spermatozoa, resulting in losses of motile sperm and damage to sperm DNA. Although sperm typically survive for days in the females of most species, sperm survival in vitro is typically only half as long, and sperm from males with poor quality ejaculates may survive for even shorter time periods in vitro. Indeed, sperm survival is suboptimal outside of the female reproductive tract.

Further, despite its proven success, still only 30% of infertile couples undergoing IVF therapy are successful in having a child. Due to the 70% failure rate of IVF procedures and the high medical bills associated with them, the majority of infertile couples choose not to go forward with IVF procedures. Other couples have moral or religion-based objections to IVF.

In light of this, it would be beneficial to provide a more successful and affordable treatment for couples who are seeking to conceive but are hindered by a diagnosis of male infertility. While most current treatment modalities focus on improving the sperm count or quality of the male, the present invention looks at the female partner as an important variable for improving the chances of conception with an infertile male partner. Indeed, since procreation involves both a male and a female, perhaps optimizing the environment in the female may improve the chances of survival of the infertile male's spermatozoa, no matter how decreased in number or viability they may be.

Prior art vaginal lubricants are generally limited to vaginally inserted artificial lubricants. Commercially available replacement vaginal lubricants, such as KY Jelly, Replens, Astroglide, and Femglide have all been shown to decrease sperm motility or even have spermicidal effects. Because of numerous medical articles reporting the adverse actions of vaginal lubricants on sperm, it is currently contraindicated for infertility patients to use any of the above types of vaginal lubricants to treat insufficiency. Such lubricants do not intravaginally capacitate sperm or intravaginally provide a medium for gradient sperm differentiation.

U.S. Pat. No. 6,322,493 and U.S. Pat. No. 6,702,733, both to Thompson and incorporated herein by reference in their entirety, teach of the topical use of menthol in combination with L-arginine as a means for treating decreased female sexual arousal. The topical menthol has two functions, initial mucous membrane vasodilatation, and secondarily as a permeability enhancer to facilitate the transport of L-arginine into the clitoral tissues to affect and generate a clitoral erection.

U.S. published patent application 2005/0244520 to Thompson, and incorporated herein by reference in its entirety, describes the reflex production of normal physiological vaginal lubrication as a treatment for decreased female sexual arousal, or female sexual dysfunction. This document defines a combination of menthol, or a related cooling compound, and L-arginine topically applied to the clitoris to evoke reflex vaginal lubrication, to treat lubrication insufficiency relative to female sexual dysfunction.

U.S. Published Patent Application 2007/0060653 to Thompson and incorporated herein by reference in its entirety, teaches the use of the topical menthol in combination with L-arginine to treat lubrication insufficiency ascribed to 75% of infertile women. This document describes how the induction of a physiological vaginal transudate by the topical clitoral application of menthol and L-arginine can support the function and viability of spermatozoa, initially in the hostile vaginal environment, and ultimately in the cervical mucus. It teaches that maximizing production of this physiological vaginal transudate will optimize spermatozoa survival and function in the female reproductive tract, thereby increasing the odds of conception in females suffering from female sexual dysfunction.

While recent advances in treating female infertility may be useful for their intended purposes, there remains an unmet need for couples suffering from infertility in which the male is diagnosed as being infertile. It would therefore be beneficial to provide a method for increasing the chances of survival in the vagina of healthy sperm produced by a male suffering from abnormal semen quality. It would also be advantageous to provide a method to minimize or prevent the damage imparted to sperm caused by methods such as in vitro sperm swim-up and capacitation techniques, centrifugal separation, freezing, or the like. It would further be beneficial to provide an in vivo method of treatment in which the male's sperm do not undergo extracorporeal handling or treatment.

SUMMARY OF THE INVENTION

The present invention is a method and composition for optimizing the chances of sperm survival within the female vagina so that successful fertilization occurs for couples suffering from male infertility. A first aspect of the invention relates to a method for optimizing sperm survival and function for human couples suffering from male infertility, the method comprising the steps of: (a) diagnosing a couple comprising a male sexual partner and a female sexual partner with male infertility wherein the male infertility is caused by abnormal sperm quality in the male sexual partner; and (b) applying a topical composition containing menthol, or a related cooling compound, directly onto the vulva of the female sexual partner prior to sexual intercourse, wherein the composition stimulates and increases vaginal lubrication and leads to the production in the female sexual partner of a vaginal transudate which supports the survival and fertilizing capability of sperm deposited by the male sexual partner.

A second aspect of the invention is a method for treating male infertility caused by abnormal semen quality, the method comprising the steps of: (a) diagnosing a couple comprising a male sexual partner and a female sexual partner with male infertility wherein the male infertility is caused by abnormal sperm quality in the male sexual partner; and (b) applying a topical composition to the vulva of the female sexual partner prior to sexual intercourse, the topical composition comprising a therapeutically effective amount of menthol which stimulates and increases the female's vaginal lubrication and leads to the production of a vaginal transudate which supports the survival and fertilizing capability of spermatozoa.

A third aspect of the invention is, in a couple comprising a male sexual partner and a female sexual partner seeking treatment for male infertility, a topical composition for application to the vulva of the female sexual partner prior to sexual intercourse, the topical composition comprising a therapeutically effective amount of menthol which stimulates and increases the female's vaginal lubrication and leads to the production of a vaginal transudate which supports the survival and fertilizing capability of spermatozoa.

While the nature and advantages of the present invention will be more fully appreciated from the following detailed description, and more particularly defined by the appended claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

As used herein, the term "abnormal semen quality" means semen having a low sperm count, impaired sperm motility, impaired sperm morphology, or impaired sperm viability. A semen specimen having a disproportionate number of spermatozoa with shape or motility defects, or an abnormally low number of spermatozoa, is classified as having abnormal semen quality. Low sperm count is a decrease in the concentration of spermatozoa to below 15 million/ml, or a total number of below 39 million. Although sexual function is typically normal in men suffering from abnormal semen quality, there is a reduced count of normal, functional spermatozoa and/or a disproportionate number of spermatozoa that are dysfunctional in either motility or morphology.

As used herein, the terms "vulva", "external female genitalia", and "external genitalia of the female sexual partner" shall be used interchangeably and include the mons pubis, the labia majora, the labia minora, the clitoris, the bulb of vestibule, the vulval vestibule, the urinary meatus, the greater and lesser vestibular glands, the vaginal opening, the pudendal cleft, and the urogenital triangle (anterior part of the perineum).

As used herein, the terms "infertility" and "subfertility" shall be used interchangeably, unless expressly stated otherwise.

As used herein, the terms "spermatozoa" and "sperm" shall be used interchangeably, unless expressly stated otherwise.

Figure 1:
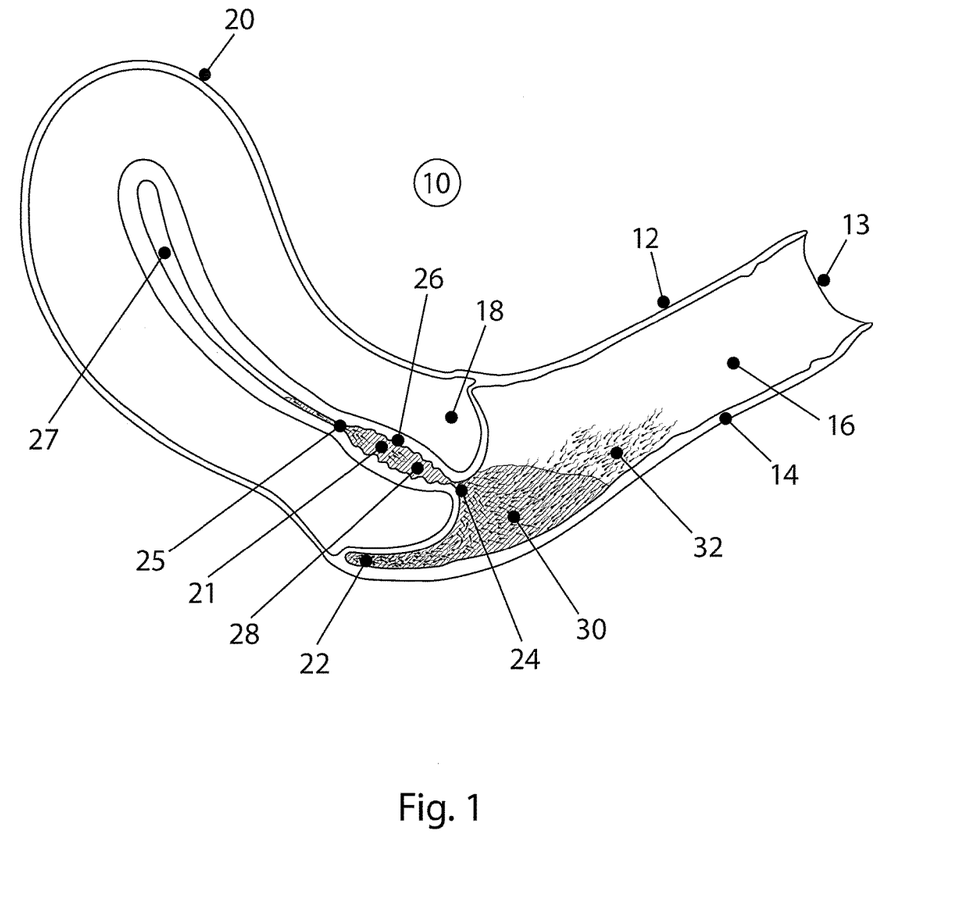
FIG. 1 is a schematic lateral view of the cervix of a female after receiving therapy via the inventive method and following sexual intercourse with an infertile male partner.
Figure 2:
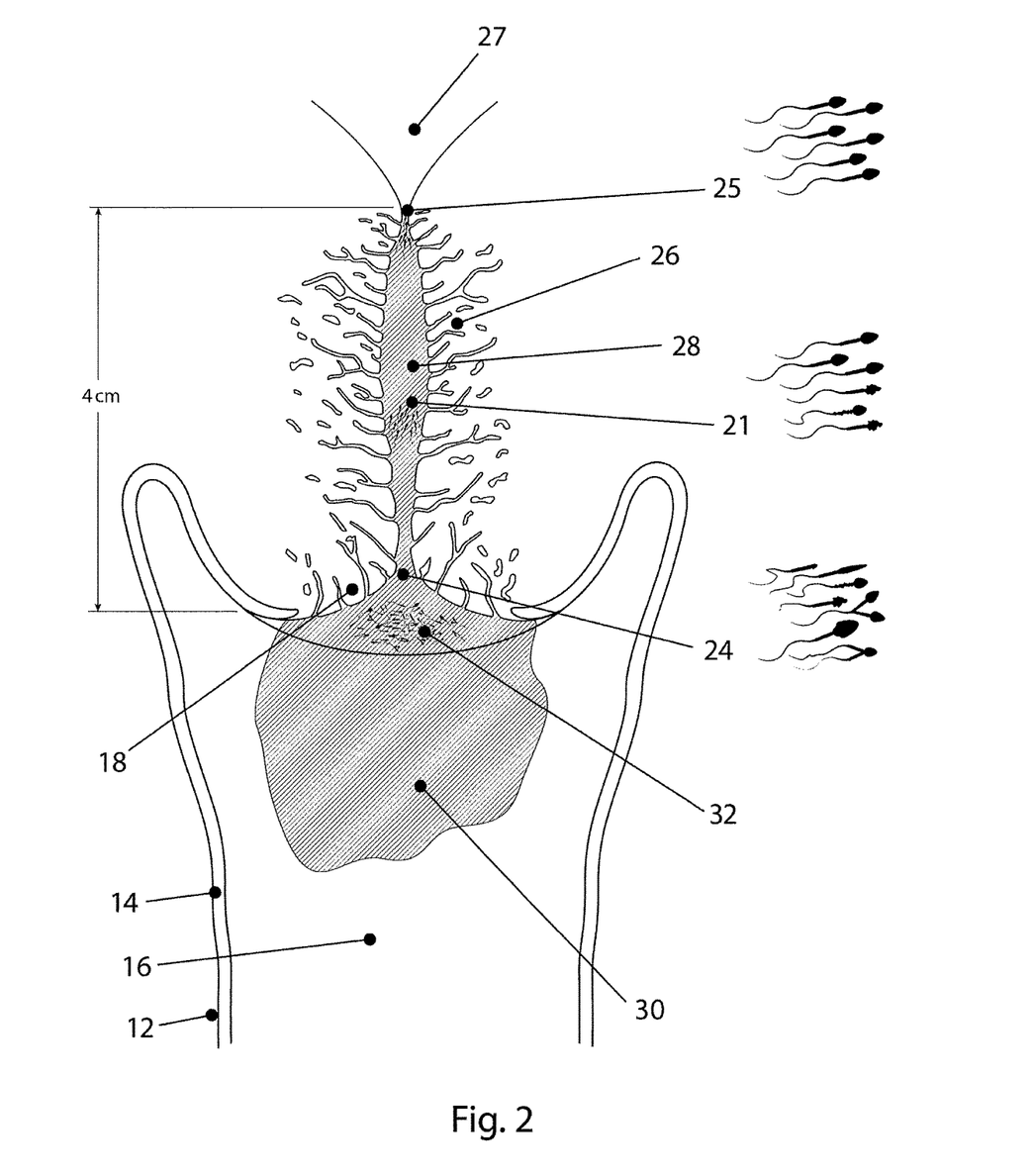
FIG. 2 is a schematic frontal view of the cervix of FIG. 1.
Figure 3:
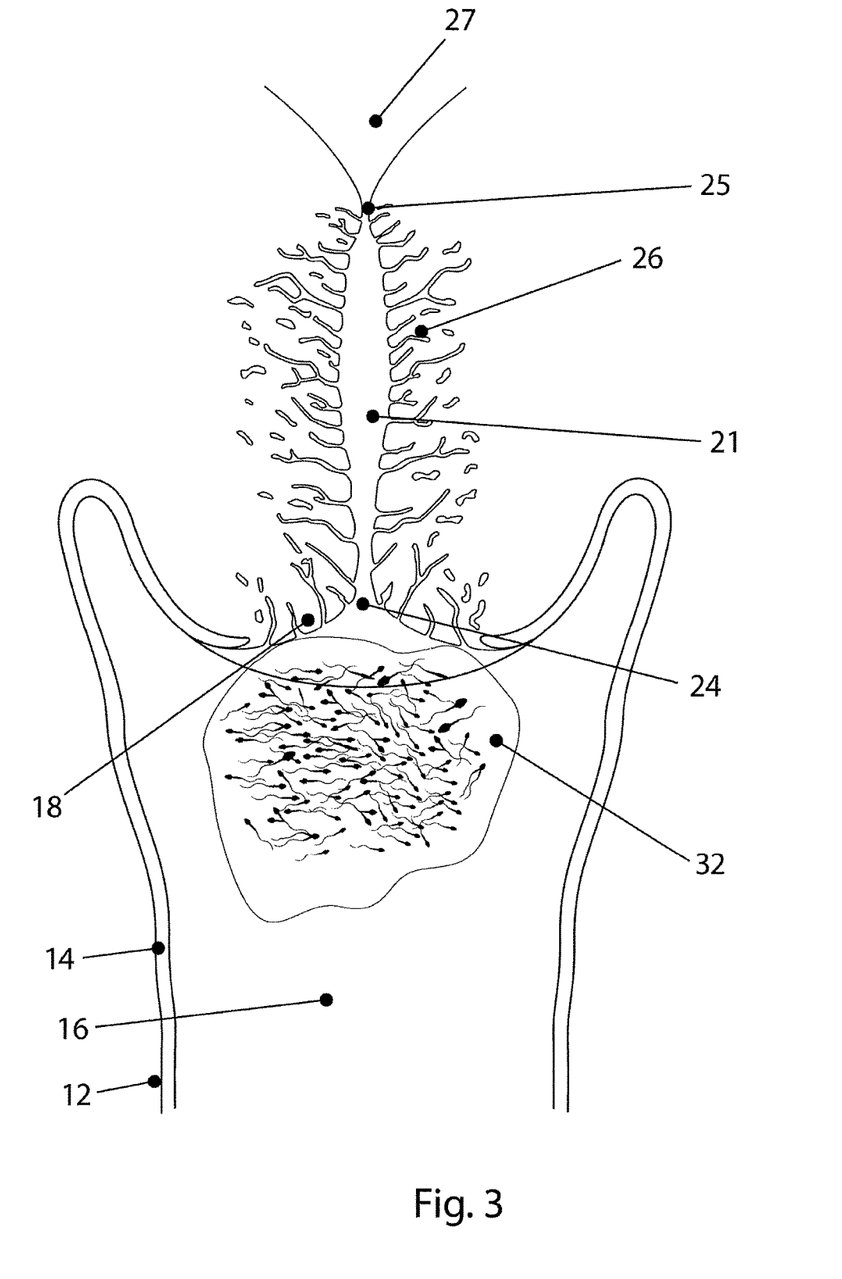
FIG. 3 is a schematic frontal view of the cervix of a female following sexual intercourse with an infertile male partner without receiving therapy via the inventive method.

FIGS. 1-3 are schematic views of the internal genitalia 10 of a human female following sexual intercourse with a male partner. The vagina 12 includes a vaginal wall 14 and a vaginal canal or lumen 16 which extends from the vaginal opening 13 to the cervix 18. The vagina 12 serves as the receptacle for the penis during sexual intercourse, and as the birth canal during labor. During sexual arousal the cervix 18 will lift upwards and the posterior vaginal fornix 22, which is a cul-de-sac of the vagina 20, can extend upwards into the body as long as necessary to receive the male penis. After intercourse, the contraction of the vagina will allow the cervix 18 to rest inside the fornix 22, which in its relaxed state is bowl-shaped, perfect for pooling of physiologic fluids (best seen in FIG. 1).

This pool of seminal fluid 32 and vaginal plasma transudate 30 typically coagulates into a loose gel within about a minute of coitus. This coagulum serves to temporarily hold the sperm at the external cervical os 24, so that the sperm can swim through the opening, and also helps to protect the sperm against the harsh environment of the vagina. The increased amount of vaginal transudate 30 produced in the female partner of a couple being treated according to the present invention leads to an increase in the amount of serum albumin present in the cervical mucus 28. This occurs by passive diffusion from an area of high concentration, the vaginal transudate 30, to an area of low serum albumin concentration, the cervical mucus 28. Thus, when the inventive method is used for treatment of such couples, the combination of semen, increased vaginal lubrication, and endocervical mucus combine to create an optimal environment for the male's abnormal spermatozoa, from which they are slowly released for ascension up the female reproductive tract to the distal fallopian tubular ampulla, ultimately leading to oocyte penetration and fertilization. With this optimized environment, the healthiest, most functional sperm are able to both diffuse into and actively swim into the cervical mucus 28 for the length of time that they remain viable.

The external cervical os 24 provides an opening which connects the lumen of the vagina 16 to the uterus 20 via the cervical canal 21. At the distal end of the cervical canal 21 the internal cervical os 25 allows spermatozoa to pass through to the uterine cavity 27 on their way to the fallopian tubes and ovaries. The cervical canal 21 contains endocervical glands 26, which are a collection of columnar epithelium from which cervical mucus 28 is secreted. Cervical mucus 28 changes in appearance and consistency throughout the menstrual cycle, but as ovulation approaches it becomes more hydrated, slippery and elastic and serves as a transport medium for sperm.

As can best be appreciated from viewing FIGS. 1 and 2, post-coitus the external cervical os 24 is both bathed by cervical mucus 28 produced by the cervical glands 26 in the cervical canal 21 and immersed in a transudate 30 produced in the vagina. The transudate 30 is also mixed with spermatozoa 32 from the male. As best seen in FIG. 1, the semen 32 and the vaginal transudate 30 are pooled in the posterior vaginal fornix 22, bathing the external cervical os 24. Cervical mucus 28 also mixes with the transudate 30 and semen 32 at the external cervical os 24.

As best seen in FIG. 2, optimal conditions exist when semen 32, vaginal transudate 30 and cervical mucus 28 are all present at the external cervical os 24 and able to mix and access the cervical canal 21. By applying a composition containing an effective amount of menthol or related cooling compound directly onto the vulva of the female sexual partner prior to sexual relations, increased vaginal lubrication is followed by increased production of the vaginal transudate 30, optimizing the environment in which the infertile male's semen 32 is deposited during sexual intercourse. This transudate 30 supplies the cervical mucus 28 with basic ions which decrease the acidity of the vaginal lumen 16. The transudate 30 also provides water which hydrates the cervical mucus 28. Human serum albumin and oxygen are also present in the vaginal transudate 30, which are required for successful sperm capacitation. This is the environment that the present invention produces, selecting for the normal, healthy sperm of the infertile male to reach the internal cervical os 25 and make their way to the uterine cavity 27 and ultimately to the fallopian tubes and oocytes for fertilization.

Sperm capacitation is the transformation of the sperm to produce flagellar (tail) whip-like motions that allows for forward propagation of the spermatozoa and the acrosome reaction. Both are initiated by the serum albumin dilation of the spermatozoa surface cholesterols. The acrosome reaction is the organization of the head of the sperm into a cap that contains enzymes to digest the cumulus oopherus, zona pellucida, and oocyte cell membrane. This digestion allows entrance of the nuclear DNA of the spermatozoa into the nucleus of the oocyte, or fertilization. The initiation of spermatozoa capacitation and acrosome reaction are quite complex, but completely dependent upon human serum albumin.

Looking again at FIGS. 1 and 2, following intercourse the abnormal semen 32 of the male suffering from infertility is pooled along with the female's vaginal transudate 30 in the posterior vaginal fornix 22. Although some semen is lost through the vaginal opening 13, typically gravity repositions the semen in a pool or reservoir in the posterior vaginal fornix 22 within minutes, with the male's sperm suspended in seminal fluid 32 and the vaginal plasma transudate 30. The cervix 18 is positioned so that it interfaces with the uppermost layer of this transudate 30 in the posterior vaginal fornix 22. The topical menthol composition stimulates the production of vaginal transudate 30 in an amount sufficient to intermix the transudate 30 with the sperm 32 deposited by the male sexual partner, as well as with the endocervical mucus 28 at the external cervical os 24. This enhanced environment aids in capacitating the most healthy of the male's abnormal sperm, and provides a swim-up function. Thus, the inventive method provides a means for the infertile male's most active, capacitated sperm to gain access to the cervix 18. The chances of fertilization by the healthiest of the male's abnormal sperm are increased when the external cervical os 24 and extruding cervical mucus 28 are immersed in this reservoir of spermatozoa/seminal fluid 32 and vaginal plasma transudate 30. Sperm both diffuse into and actively swim from this reservoir 30, through the cervical os 24 and into the cervical mucus 28 for the length of time that the spermatozoa remain viable in the vagina, providing a constant supply of capacitated spermatozoa to the cervical canal 21 for one to three days following coitus.

The right side of FIG. 2 shows blown-up representations of pools of the male's sperm at various locations as they traverse the cervix 18. Note that the length of the cervical canal 21 is about 4 cm from the external cervical os 24 to the internal cervical os 25 (see left side of FIG. 2). At the level of the external cervical os 24, sperm are shown which include a decreased amount of normal, healthy sperm and a disproportionate amount of abnormal or immature sperm, or sperm having abnormal morphology. As the capacitated sperm swim up through the cervical canal 21, there is shown a greater proportion of normal sperm having made it this far, along with a few remaining abnormal sperm. When the sperm reach the internal cervical os 25, most if not all of the remaining sperm are healthy and normal. Thus, the 4 cm travel distance from external cervical os 24 to internal os 25 serves to create a differential gradient through which the strongest, healthiest sperm can swim up to the top and increase their chances of fertilization. The increased production of vaginal transudate 30 which results upon practice of the inventive method therefore provides a medium for gradient sperm differentiation in the vagina and cervix.

In contrast, FIG. 3 shows the environment typically present in the female vagina when the inventive therapeutic composition and method is not employed. It can be appreciated that, compared to the optimized environment shown in FIGS. 1 and 2, the environment provided in FIG. 3 does not include the vaginal transudate 30 produced by the practice of the inventive method and use of the menthol composition disclosed herein. As a result, the semen 32 does not have the basic ions, water, serum albumin and oxygen needed for proper capacitation and swim up. While cervical mucus may be present in the cervical canal 21, the absence (or inadequate amount) of the vaginal transudate 30 does not allow for sperm capacitation, and thus the sperm are not able to swim at all, much less up through the cervical canal 21 and through the internal cervical os 25 to the intrauterine cavity 27.

Abnormal sperm quality in combination with inadequate vaginal lubrication can cause infertility. The menthol-stimulated vaginal plasma transudate 30 that is generated by use of the inventive method compensates for lubrication insufficiency that may be present in the female sexual partner of the infertile male. The inventors have found that topical menthol applied to the vulva (including the clitoris) increases lubrication for 80% of all women, and 90% of women over 35. Since most infertility is a combination of female and male factors, the production of this vaginal transudate 30 can aid conception rates of both infertile males and females. As FIG. 3 reveals, when menthol-stimulated vaginal transudate lubrication is not present, not only is there no medium with enough albumin present to capacitate the sperm, there also is no pool of transudate bathing the external cervical os 24. Therefore the sperm, even if they somehow are able to be capacitated, have little or no protective and nourishing substrate in which they can swim up through the external os 24 and into the cervical canal 21. The odds of fertilization are thus extremely low.

The use of the menthol composition on the external genitalia initiates enhances blood flow and vasocongestion in the vagina and vulva, leading to engorgement of the female genitalia and blood plasma leakage due to an influx of blood into the vascular plexus of the vulva. This plasma transudate diffuses across the vaginal mucosa and into the lumen 16 of the vagina, leading to the formation of the transudate 30 which lubricates the vaginal walls 14. At either side of the vaginal opening 13 are the Bartholin's glands (not shown) which produce small amounts of mucus to keep the inner labia moist during periods of sexual arousal. Increased lubrication initiated by the menthol compound and assisted by sexual arousal create the vaginal transudate 30 which can support, nurture, and optimize sperm survival and function.

Important functions of the vaginal transudate 30 include decreasing vaginal acidity, increasing vaginal oxygenation, increasing cervical hydration, and providing a source of albumin for the cervical mucus 28 to initiate capacitation of sperm 32. The amount of transudate produced by the female partner is enhanced by the application of the compound disclosed herein, but is also dependent upon the level of sexual arousal prior to and during intercourse, as well as the levels of the hormones estrogen and progesterone currently circulating within the female. However, in situations in which the male suffers from abnormal semen quality, sexual arousal and elevated hormone levels alone may not be enough to create a suitable environment for the abnormal spermatozoa. Application of the inventive compound containing menthol is thus deemed a requisite step of the inventive method. The increased amount of vaginal transudate 30 produced in the female partner of a couple being treated according to the present invention leads to an increase in the amount of serum albumin present in the cervical mucus 28. With this optimized environment, the healthiest, most functional of the infertile male partner's sperm are able to actively swim into the cervical mucus 28 at the external cervical os 24, traverse the cervical canal 21, and pass through the internal cervical os 25 to the uterine cavity 27 and ultimately to the oocyte.

The vaginal transudate 30 contains all of the components of human serum albumin except the coagulation factors. This is important because albumin is essential for sperm capacitation, a transformation of the sperm that allows the sperm to both access and fertilize the oocyte. The albumin in the vaginal transudate will, like the ions for pH determination, the water for hydration, and the dissolved oxygen for oxygenation, passively diffuse from the vaginal lumen 16, through the opening of the cervical os 24 and into the cervical canal 21, mixing with the cervical mucus 28. This diffusion from the vaginal canal 16 to the cervical canal 21 is dependent upon the volume of vaginal plasma transudate 30 and the volume of cervical mucus 28. The more abundant the plasma transudate 30, the more efficient will be the movement of the ions, water, oxygen, and human serum albumin through the opening of the cervical os 24 and into the cervical canal 21, for mixing with the cervical mucus 28. Human serum albumin is perhaps the most important of these factors because only a capacitated sperm can fertilize an oocyte and establish pregnancy. Nevertheless, an increase in all of these factors is desired and is a goal of the present invention, in order to aid the infertile male's sperm to achieve fertilization.

Figure 4A:
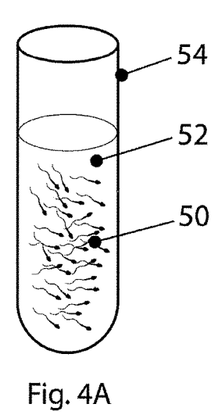
FIGS. 4A-E are schematic views of typical in vitro laboratory procedures used for sperm capacitation and differentiation.
Figure 4B:
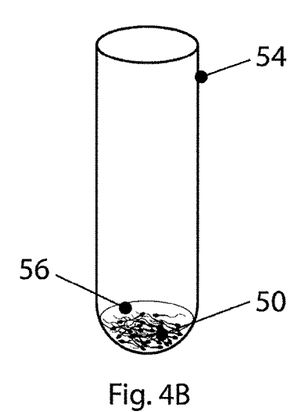
Figure 4C:
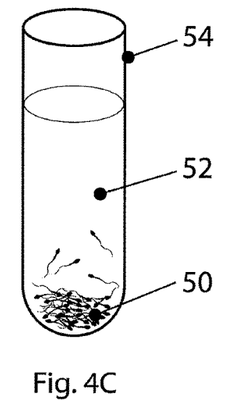

Looking at FIGS. 4A-4E, the typical laboratory (in vitro) procedures that are used for sperm capacitation and differentiation are shown. Specifically, FIGS. 4A and 4B show the initial step of capacitation, in which the male's semen, containing an initial sperm sample 50 of all shapes, sizes and numbers, is suspended in a solution 52 filling a containment vessel such as a test tube 54. For example, Ham's F-10 includes 10% serum albumin, and is a typical solution 52 used for this purpose. Just like human serum albumin in the cervical mucus, the albumin in the solution 52 completely dissolves away the cholesterol coating on the spermatozoa, thus permitting the tails thereof to initiate their whip-like action. This loss of cholesterol is a necessary element of an assortment of interrelated membrane changes leading to capacitation in human spermatozoa. Hyperactive motility is one of the characteristic changes seen as a result of capacitation. Sperm motility becomes more vigorous, and the sperm develops a wider amplitude of lateral head displacement, a marked increase in flagellar beating, and a curved and tortuous trajectory. Although the functional significance of these changes remains unclear, they may facilitate sperm transit through the oviduct and provide the necessary force needed to penetrate the granulosa cell layer and zona pellucida surrounding the ovum. Sperm that display these hyperactive patterns tend to be those with normal morphology.

Figure 4D:
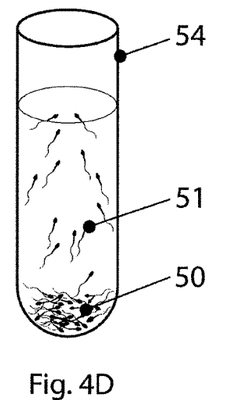
Figure 4E:
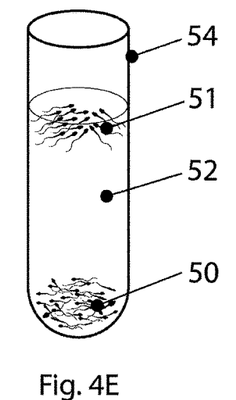

The sperm 50 shown in FIG. 4A are typically incubated for one hour at 37° C., which allows all of the spermatozoa to capacitate and become mobile. The solution is then centrifuged, and after centrifugation the initial sperm capacitation media is discarded. See FIG. 4B, showing a pellet 56 containing the initial sample of sperm 50. Fresh solution 52, such as Ham's F-10/10% serum albumin media as described above, is then added as shown in FIG. 4C, and the sperm 50 of all shapes, sizes and numbers are incubated once again for several hours at 37° C. As shown in FIG. 4D, this incubation allows for the healthy, normal sperm 51 of the initial sperm sample 50 to swim out of the centrifugation pellet and up to the top of the containment vessel 54. This allows for a differential gradient swim-up typically of only motile, normal sperm 51. As illustrated in FIG. 4E, the sperm swim-up isolates a layer of normal motile sperm 51 at the top of the solution 52 in the test tube 54. The inferior sperm, immature, abnormal forms, and the chromosomally abnormal sperm of the initial sample 50 remain at the bottom of the test tube.

In contrast to the laboratory procedure for in vitro sperm capacitation and swim up described above, the present invention provides an in vivo sperm selection method including sperm capacitation and swim up for treatment of male infertility. A preferred embodiment of the invention is intended for couples, specifically a male sexual partner and a female sexual partner, who are seeking treatment for infertility in which male infertility is the primary causative factor, and primarily in which the cause of the male infertility is abnormal sperm quality. The inventive method works by stimulating and increasing intercourse-related vaginal lubrication in the female partner, which leads to an increased production of the vaginal transudate noted above. This transudate allows for capacitation and sperm swim-up through the cervical canal, and is crucial to the survival and function of sperm deposited within the vaginal lumen of the female partner.

The inventive method preferably includes an initial diagnosis of male infertility, and specifically abnormal semen quality in the male partner. Low sperm count, impaired sperm motility, impaired sperm morphology, and impaired sperm viability are all elements of abnormal semen quality. These conditions are amenable to the inventive method because the male typically remains capable of making functional sperm, albeit not as viable or as many as is normally needed to be successful with fertilization. The inventive method renders the environment of the vaginal canal 16 more conducive to the survival of the infertile male's semen 32, specifically by stimulating the production of the vaginal transudate 30 in an amount sufficient to intermix the transudate 30 with the sperm 32 deposited by the male sexual partner, as well as with cervical mucus 28 that is present at the external cervical os 24. This enhanced environment aids in capacitating the most healthy of the male's abnormal sperm, and provides an in vivo swim-up function similar to that seen with in vitro methods (see, e.g. FIG. 2 and FIGS. 4A-4E). Further, the transudate 30 makes the vaginal canal less acidic, provides water to hydrate the cervical mucus, and provides human serum albumin and oxygen to the mucus 28 and the semen 32, which is valuable to sperm for capacitation and swim up of the most healthy, motile sperm.

A preferred composition for use with the inventive method contains menthol for topical application to the external female genitalia. The external female genitalia (not shown) are collectively referred to as the vulva. The mons pubis is the pad of fatty tissue that covers the pubic bone below the abdomen but above the labia. The mons is sexually sensitive in some women and protects the pubic bone from the impact of sexual intercourse. The labia majora are the outer lips of the vulva, pads of fatty tissue that wrap around the vulva from the mons to the perineum. These labia are usually covered with pubic hair, and contain numerous sweat and oil glands. The labia minora are the inner lips of the vulva, thin stretches of tissue within the labia majora that fold and protect the vagina, urethra, and clitoris. Both the inner and outer labia are quite sensitive to touch and pressure. The clitoris is a small body of spongy tissue that is highly sexually sensitive. Only the tip or glans of the clitoris shows externally, but the organ itself is elongated and branched into two forks, the crura, which extend downward along the rim of the vaginal opening toward the perineum. The clitoral glans or external tip of the clitoris is protected by the prepuce, or clitoral hood, a covering of tissue similar to the foreskin of the male penis. During sexual arousal the clitoris typically extends and the hood retracts to make the clitoral glans more accessible.

In a preferred embodiment of the invention, the inventive composition includes a cooling compound such as menthol at a concentration of between 0.01% and 1.00%, and more preferably 0.35%, the remainder being a pharmacologically suitable substrate. The composition can be applied directly onto the external genitalia of the female prior to and during sexual relations, which stimulates and increases vaginal lubrication and leads to the production of a vaginal transudate in the female sexual partner. This vaginal transudate contains basic ions, water, oxygen, human serum albumin, among other useful compounds, and supports the survival and fertilizing capability of the spermatozoa deposited by the male sexual partner during subsequent sexual intercourse.

A list of cooling compounds useful in the inventive composition includes menthol or any related cooling agent, including the following: peppermint oil, cornmint oil, eucalypus oil, citronella oil, camphor oil, cinnamon oil, a menthol analog or derivative with cooling properties selected such as neo-centhol, menthone, iso-menthone, menthyl acetate, menthyl isovalerate, menthyl lactate, para-menth-1-en-3ol, piperitone, menthol ethylene glycol carbonate, menthol 1- and 2-propylene glycol carbonate, menthone 1,2-glycerol ketal, and mono-menthyl succinate.

The initial step of the inventive method, which involves the diagnosis of the infertile male sexual partner as having abnormal semen quality, should include a medical workup just like any other workup for a medical illness. A thorough history should be performed, followed by a physical examination and any appropriate diagnostic testing. Integrating the history, physical examination, semen analysis, and endocrine profile are steps toward establishing the diagnosis of abnormal semen quality. By utilizing this systematic testing, patient's can be distinguished as having abnormalities of sperm quantity and quality, versus other causes of male infertility. During this process, an effort can be made to identify any underlying conditions and harmful exposures leading. The most important and pivotal aspect of the initial laboratory evaluation is the semen analysis. It is recommended that at least two semen samples be obtained with similar abstinence periods of 3 to 7 days. It is possible to have wide variations in semen parameters between specimens from the same patient. For example, sperm density may increase for the first few days of abstinence before a semen analysis, but other parameters such as sperm motility and morphology may remain unchanged.

While it may be true that a man with azoospermia is considered sterile, there is a wide range of overlap between semen parameters of fertile men compared to infertile men. The World Health Organization (WHO) has published reference values for semen including volume, pH, sperm concentration, total sperm count, motility, morphology, and other parameters. Medical professionals and reproductive specialists have increasingly utilized these reference values in the evaluation of the infertile couple. Semen samples should be obtained correctly by either masturbation or ejaculation into a specialized, non-latex, spermicidal-free collection condom. Collection of the sample can be performed in the office, or it may be collected at home and brought in for processing. In the latter case, the sample must be stored at room temperature and delivered within an hour of collection.

Once abnormal semen quality is confirmed as a potential cause of the male's infertility, the next step can be taken of optimizing the environment in which the infertile male's sperm are deposited during sexual intercourse. Applying a composition containing menthol or a related cooling compound directly onto the external genitalia of the female sexual partner, including the clitoris, prior to sexual relations is done in order to stimulate and increase vaginal lubrication in the female prior to and during sexual relations. Increased lubrication results in an increased amount of vaginal transudate in the female sexual partner. The intentional production of vaginal transudate by application of the menthol-containing compound can improve the chances of the male's decreased number of functional sperm surviving within the vagina, as well as improving the chances that these sperm will undergo capacitation and successful swim up through the cervical canal to the uterus. The inventive method thus improves the chances of successful fertilization by one of the few functional sperm produced by an infertile male. The inventive treatment method is advantageous and desirable because it bypasses the step of treating spermatozoa outside of the human body, and therefore increases the chances of survival of a larger number of functional sperm as compared to prior methods.

While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. The invention in its broader aspects is therefore not limited to the specific details, representative system and method, and illustrated examples shown and described. Accordingly, departures may be made from such details without departing from the scope of the invention.

What is claimed is:

1. A method for optimizing sperm survival and function for human couples suffering from male infertility, the method comprising:
   (a) diagnosing a couple comprising a male sexual partner and a female sexual partner with male infertility, wherein the male infertility is caused by a reduced number of normal, functional sperm in the male sexual partner; and
   (b) applying a topical composition containing menthol to the vulva of the female sexual partner prior to sexual intercourse, wherein the composition stimulates and increases the female's vaginal lubrication and leads to the production in the female sexual partner of a vaginal transudate which supports the survival and fertilizing capability of the reduced number of normal, functional sperm deposited by the male sexual partner.

2. The method of claim 1, wherein the amount of menthol in the topical composition is between 0.01% and 1.00%.

3. The method of claim 1, wherein the amount of menthol in the topical composition is 0.35%.

4. The method of claim 1, wherein the topical composition is applied to the female vulva both prior to and during sexual intercourse.

5. The method of claim 1, wherein the topical composition stimulates the production of vaginal transudate in an amount sufficient to intermix the transudate with the reduced number of normal, functional sperm deposited by the male sexual partner and with endocervical mucus at the external cervical os.

* * * * *